US00RE44596E

(19) United States
(12) Reissued Patent
Stroun et al.

(10) Patent Number: US RE44,596 E
(45) Date of Reissued Patent: Nov. 12, 2013

(54) METHOD FOR THE DETECTION OF CANCER

(75) Inventors: Maurice Stroun, Geneva (CH); Philippe Anker, Geneva (CH)

(73) Assignee: Guardant Health, Inc., Redwood City, CA (US)

(21) Appl. No.: 13/447,104

(22) Filed: Apr. 13, 2012

Related U.S. Patent Documents

Reissue of:
(64) Patent No.: 7,700,286
Issued: Apr. 20, 2010
Appl. No.: 11/336,780
Filed: Jan. 23, 2006

(30) Foreign Application Priority Data

Apr. 6, 2005 (EP) ..... 05007508

(51) Int. Cl.
*C12Q 1/68* (2006.01)
*C12P 19/34* (2006.01)

(52) U.S. Cl.
USPC ..... 435/6.1; 435/6.11; 435/6.12; 435/6.14; 435/91.1; 435/91.2; 435/91.21; 435/91.5; 435/91.51

(58) Field of Classification Search
None
See application file for complete search history.

(56) References Cited

U.S. PATENT DOCUMENTS

| | | | |
|---|---|---|---|
| 6,329,179 | B1 | 12/2001 | Kopreski |
| 6,916,634 | B2 | 7/2005 | Kopreski |
| 6,939,671 | B2 | 9/2005 | Kopreski |
| 7,767,423 | B2 | 8/2010 | Kopreski |
| 7,785,842 | B2 | 8/2010 | Kopreski |

FOREIGN PATENT DOCUMENTS

| | | | |
|---|---|---|---|
| EP | 1 158 055 | | 11/2001 |
| EP | 1158055 | A1 | 11/2001 |
| WO | WO 97/35589 | | 10/1997 |
| WO | WO 97/35589 | A1 | 10/1997 |
| WO | WO 01/90409 | | 11/2001 |
| WO | WO 01/90409 | A1 | 11/2001 |

OTHER PUBLICATIONS

Anker, et al. Detection of circulating tumour DNA in the blood (plasma/serum) of cancer patients. Cancer Metastasis Rev. 1999;18(1):65-73.
Anker, et al. Progress in the knowledge of circulating nucleic acids: plasma RNA is particle-associated. Can it become a general detection marker for a cancer blood test? Clin Chem. Aug. 2002;48(8):1210-1.
Chan, et al. Plasma Epstein-Barr virus DNA and residual disease after radiotherapy for undifferentiated nasopharyngeal carcinoma. J Natl Cancer Inst. Nov. 6, 2002;94(21):1614-9.
Chen, et al. Telomerase RNA as a detection marker in the serum of breast cancer patients. Clin Cancer Res. Oct. 2000;6(10):3823-6.
Dasi, et al. Real-time quantification in plasma of human telomerase reverse transcriptase (hTERT) mRNA: a simple blood test to monitor disease in cancer patients. Lab Invest. May 2001;81(5):767-9.
Fleischhacker, et al. Detection of amplifiable messenger RNA in the serum of patients with lung cancer. Ann N Y Acad Sci. Sep. 2001;945:179-88.
Hasselmann, et al. Detection of tumor-associated circulating mRNA in serum, plasma and blood cells from patients with disseminated malignant melanoma. Oncol Rep. Jan.-Feb. 2001;8(1):115-8.
Kopreski, et al. Detection of tumor messenger RNA in the serum of patients with malignant melanoma. Clin Cancer Res. Aug. 1999;5(8):1961-5.
Nawroz, et al. Microsatellite alterations in serum DNA of head and neck cancer patients. Nat Med. Sep. 1996;2(9):1035-7.
Rykova, et al. Breast cancer diagnostics based on extracellular DNA and RNA circulating in blood. Biochemistry (Moscow) Supplement Series B: Biomedical Chemistry. 2008; 2(2):208-213.
Silva, et al. Detection of epithelial messenger RNA in the plasma of breast cancer patients is associated with poor prognosis tumor characteristics. Clin Cancer Res. Sep. 2001;7(9):2821-5.
Silva, et al. Detection of epithelial tumour RNA in the plasma of colon cancer patients is associated with advanced stages and circulating tumour cells. Gut. Apr. 2002:50(4):530-4.
Wong, et al. New markers for cancer detection. Curr Oncol Rep. Nov. 2002;4(6):471-7.
Wong, et al. Quantitative correlation of cytokeratin 19 mRNA level in peripheral blood with disease stage and metastasis in breast cancer patients: potential prognostic implications. Int J Oncol. Mar. 2001;18(3):633-8.
Wong, et al. Quantitative relationship of the circulating tumor burden assessed by reverse transcription-polymerase chain reaction for cytokeratin 19 mRNA in peripheral blood of colorectal cancer patients with Dukes' stage, serum carcinoembryonic antigen level and tumor progression. Cancer Left. Jan. 10, 2001;162(1):65-73.
Philippe Anker et al., "Circulating Nucleic Acids in Plasma and Serum as a Noninvasive Investigation for Cancer: Time for Large-Scale Clinical Studies?", International Journal of Cancer, 2003, pp. 149-152, XP 002275956.
Carsten Goessl, "Diagnostic Potential of Circulating Nucleic Acids for Oncology", Expert Review of Molecular Diagnostics, 2003, vol. 3, No. 4, p. 431-442, XP009052512.
Javier Silva et al., "RNA is More Sensitive than DNA in Identification of Breast Cancer Patients Bearing Tumor Nucleic Acids in Plasma", Genes, Chromosomes & Cancer, vol. 35, No. 4, 2002, pp. 375-376, XP009052544.

*Primary Examiner* — Eileen B O Hara
(74) *Attorney, Agent, or Firm* — Wilson Sonsini Goodrich & Rosati

(57) ABSTRACT

The present invention relates to a method for the diagnosis and/or the follow up of the evolution of cancer, which includes the analysis and quantification of over expressed and amplified genes in the plasma/serum of cancer patients or persons suspected to harbor cancer. This is achieved by analyzing together the amount of DNA and RNA of certain genes in the plasma/serum of cancer patients that are the reflection of a gene amplification and/or a gene over expression in comparison to healthy controls.

46 Claims, 3 Drawing Sheets

METHOD FOR THE DETECTION OF CANCER

Matter enclosed in heavy brackets [ ] appears in the original patent but forms no part of this reissue specification; matter printed in italics indicates the additions made by reissue.

The present invention describes a method of diagnosis and/or follow up of the evolution of most types of cancer, for instance after a chemotherapy or after an operation.

It is known that diagnosis and follow up of the evolution of cancer are done, besides direct observation of the tumors, by biopsy analysis or in the case of blood malignancies by analysis of the bone marrow. This implies either a surgical intervention or an invasive test such as a biopsy or a bone marrow aspiration. Now, without taking into account the disagreeable or even dangerous aspect of such methods it has been observed that they could moreover not be very precise.

Conventional methods of diagnosis are not very satisfactory. As an example, colorectal cancer screening presently relies on fecal occult blood testing (FOBT) which is both insensitive and non-specific. In contrast, flexible sigmoidoscopy is sensitive and specific for early distal disease but is both invasive and insensitive for proximal disease. Furthermore, barium enema is relatively sensitive and specific but requires colonic preparation, radiation and a day off work, while total colonoscopy is highly sensitive and specific but is also invasive and expensive.

The situation appears little better for other cancers. No reliable test is available for early detection of lung cancer, with computerized tomography being the most reliable tool.

An important strategy to reduce mortality from breast cancer is the introduction of mammographic screening in an attempt to detect cancers at an asymptomatic and pathologically early stage. Although several studies indicate that mass screening is a useful strategy for reducing breast cancer mortality, there are a number of disadvantages associated with this form of cancer screening. These include a high rate of false positive tests, frequent false negative tests and the enormous public health costs involved. Thus, when the benefits of mammographic screening are weighed against its costs and other disadvantages, it is perhaps not surprising that this form of screening has engendered an enthusiastic and contentious debate over the past 20 years.

Finally, development of conventional protein tumor markers, such as carcinoembryonic antigen (CEA) and alpha-fetoprotein (AFP), along with the widely used prostate specific antigen (PSA) was driven largely by the introduction of new methods for quantifying small amounts of circulating proteins. However, sensitivity and specificity shortcomings with these assays remain to be overcome.

The aim of this invention consists therefore in providing a method of diagnosis and/or follow up of the evolution of most types of cancer which would be, on one hand, more precise and trustworthy and, on the other hand easier to perform without implying an invasive test for the patient.

Small amounts of free DNA circulate in both healthy and diseased human plasma or serum, and increased concentrations of plasma or serum DNA are present in cancer patients. The present inventors were the first to demonstrate that this DNA extracted from the plasma of cancer patients has tumor related characteristics. They include decreased strand stability, oncogene and tumor suppressor gene mutations, microsatellite alterations, and gene hypermethylation. This has led to suggest that a non-invasive diagnostic test for cancer might be feasible using these molecular techniques.

Using essentially similar molecular techniques, tumor related mRNA have been detected in the plasma of cancer patients. These RNA markers are the result of an over expression of some genes in the cancer cells and may be found in increased quantities in the plasma/serum of cancer patients compared to healthy controls.

Now this over expression of genes is often accompanied by an amplification of the same gene in the cancer cells, and the present inventors have found that this amplification can be seen subsequently in the plasma/serum of the patient. It should be stressed that this amplification is independent of the fact that there is, as mentioned above, usually more plasma/serum DNA in cancer patients than in healthy controls.

The present inventors have therefore developed a cancer detection assay in plasma/serum measuring by adding and comparing the amount of DNA and RNA of certain genes in the plasma/serum of cancer patients that are the reflection of a gene amplification and a gene over expression. Thus gene amplification (seen by more DNA) and gene over expression (more RNA) are linked.

Consequently, the object of the present invention, reaching the above-mentioned aim, is consisting of a method for the diagnosis or the follow up of the evolution of cancers which comprises measuring together gene over expression (RNA) and gene amplification (DNA) in the bodily fluids of patients suspected to harbor cancer on any gene that is both amplified and over expressed in cancer cells and comparing to healthy controls.

More particularly, RNA and DNA are extracted from a bodily fluid, such as plasma, serum, sputum, saliva, etc, purified and amplified, and the over expressed RNA and amplified DNA are analyzed and compared to a unique house keeping gene.

As examples, the genes analyzed can be selected from hTERT, hTR, TEP1, MYCN, MYCC, ErbB2, Her2, Her2/Neu, Her1, Cyclin A and D1, ABL, SKP2, ETV6 (TELgene), MGC2177, PLAG1, PSMC6P and LYN.

Preferably, the nucleic acids are amplified by reversed transcriptase chain reaction (RT-PCR) and are analyzed by gel coloration, by radioactive immunological technique (RIA), by enzyme linked immunosorbant test (ELISA) or by a microchip test (gene array), and possibly quantified by any method for nucleic acid quantification.

The quantification of RNA and DNA can advantageously be carried out by real time PCR, such as "TAQMAN™", or on capillaries "LIGHTCYCLER™", or real time PCR and RT PCR of any company.

Furthermore, the genes analyzed may be compared to a reference nucleic acid extract (DNA and RNA) corresponding to the expression (RNA) and quantity (DNA) of a unique house keeping gene, or to a reference RNA corresponding to the expression of a house keeping coding gene, or to a reference DNA corresponding to a unique gene, or may be estimated in reference to a standard curve obtained with nucleic acids of a cell line.

In the following description of the present invention, telomerase RNA and DNA have been chosen as example, since telomerase activity is enhanced in 85 to 100% of cancers. But it must be stressed that the present invention is valid for all genes, and specially oncogenes that have been reported to be both amplified and over expressed in many cancers and cancer cell lines, for instance MYCN in neuroblastoma, ErbB2 in esophagal, breast and ovarian cancer, Her2, Her2/Neu and Her1 in breast and Her2/Neu in lung, Cyclin A an D1 in colorectal or laryngeal cancer, ABL in leukemias and lymphomas, SKP2 in non small cell lung cancer, ETV& (TEL-gene) in myelodysplastic syndrome. These are some of the most studied, but many others have been reported, such as MGC2177, PLAG1, PSMC6P, and LYN.

To illustrate the present invention, the hTERT gene was used, which codes for the reverse transcriptase of the telomerase ribonucleoprotein.

Telomerase is a ribonucleoprotein enzyme that synthesizes repeated telomeric sequences at chromosomal ends. The telomeres protect the chromosomal ends and at each cell division these telomeres are shortened. Telomerase composed of an RNA template (hTR) and a reverse transcriptase enzyme (hTERT) plus associated proteins such as TEP 1 that synthesizes these telomeres.

The activity of this enzyme has become an accepted indicator for the diagnosis and the prognosis of most malignant tumors. The expression of human telomerase RNA (hTR) or of the reverse transcriptase enzyme of the RNA telomerase (hTERT) or of the associated protein (TEP1) has been measured during the progression of several types of tumors. This has enabled the establishment of a correlation between this expression (the amount of RNA) and telomerase activity. Most cancers and immortalized cell lines have a high telomerase activity that reflects a mechanism that escapes normal aging regulations. We have a patent in Europe and a pending patent in the US for the measurement of the amount of mRNA in the plasma/serum coding for hTERT and TEP1.

Now, an amplification of the genes (DNA) coding for telomerase subunits (especially hTERT) has been observed in cancer cell lines and in different kinds of cancers. The present inventors have further observed an amplification of the hTERT gene in the plasma of cancer patients.

Although RNA components and mRNA coding for telomerase are cellular components, it was observed that, surprisingly, these components could be also found in an extracellular form in plasma or serum.

Indeed when both nucleic acids are extracted and amplified, the difference between the healthy controls and the cancer patients is surprisingly higher.

To sum up the method, the present inventors have shown an increased amount of hTR, hTERT and TEP1 RNA in the plasma or serum of persons suffering from breast, ovarian, head and neck, pancreatic, liver, stomach or colon cancer while these products have been shown to be absent in the blood of healthy persons. Moreover DNA coding for telomerase components in particular for hTERT can also be found in greater amounts (amplified) in the plasma of cancer patients than in healthy controls. It is known since a long time that there is often more DNA in the plasma of cancer patients than in the plasma of healthy controls (this has been demonstrated by measuring the amount of beta-globin for instance), but hTERT DNA yields even more than what could be expected, giving evidence of an amplification of this gene.

More precisely, the method of diagnosis according to the invention consists in extracting the nucleic acids (RNA and DNA) from the plasma or the serum of the blood, purifying it and amplifying it in order to establish the presence and the quantity of the product made in this case by the reverse polymerase chain reaction (RT-PCR) representing both RNA and DNA of components hTERT. This shall be done in a comparative manner between the plasma or serum of a person suspected of malignancy and the plasma or serum of a healthy person or of a control suffering from a non-malignant disease.

The amplification product of the DNA and of the RNA components transcribed into DNA by RT-PCR are detected and quantified. This can be done by any nucleic acid quantification method.

Similarly, any technique of extraction of purification and of amplification of the nucleic acids (DNA and RNA) in the plasma or the serum may be used.

The present invention will now be illustrated in a non-limitative manner by the following example related to the diagnosis of some cancers using hTERT DNA and RNA quantification.

EXAMPLE

Diagnosis of different cancers by the detection of amplified hTERT DNA and over exypressed hTERT RNA in the plasma or serum of the blood.

Blood samples (2 ml) were collected in EDTA tubes prior to surgery or treatment on patients bearing small malignant breast tumors or on patients suffering of head and neck, colorectal, pancreatic and liver cancer. Blood was taken in the same way as healthy volunteers for controls.

To guarantee good quality plasma nucleic acids, the whole blood samples should be centrifuged as soon as possible. If the centrifugation cannot take place immediately, the blood samples should be stored at 4° immediately after blood collection and centrifuged within 6 hours. The blood samples at 1,600 g for 10 min at 4° C. The plasma was transferred into new tubes taking care not to disturb the buffy coat layer. A second round centrifugation of the plasma was performed at 16,000 g for 10 min at 4° C. The plasma was finally transferred into new tubes taking care not to disturb the underlying cell pellet and stored if necessary at −70°.

RNA and DNA were extracted using a commercially available kit (Ultrasens viral kit from Qiagen), which extracts DNA as well as RNA, according to manufacturers instructions.

The primers and TAQMAN™ probe for hTERT were located on one exon and which would yield both RNA and DNA:

```
F:                                          (SEQ ID NO: 1)
5'-ACC GTC TGC GTG AGG AGA TC-3';
R:                                          (SEQ ID NO: 2)
5'-CCG GTA GAA AAA AGA GCC TGT TC-3'
and the PROBE
                                            (SEQ ID NO: 3)
5'Fam -TGT ACG TCG TCG AGC TGC TCA GGT CTT T-3'
TAMRA.
```

As reference for RNA and DNA we used the beta-Globin gene on exon 2: forward primer: 5' CTGCTGGTGGTCTACCCTTG 3' (SEQ ID NO: 4); Reverse primer: 5' CCTGAAGTTCTCAGGATCCA 3' (SEQ ID NO: 5); and Hybridization probe:5'Fam. CTCCTGATGCTGTTATGGGCAACCCT 3 TAMRA' (SEQ ID NO: 6) which would yield both RNA and DNA or the GAPDH gene on exon 8: Forward primer 5'GTGGACCTGACCTGCCG3' (SEQ ID NO: 7); Reverse primer 5' GGAGGAGTGGGTGTCGC 3' (SEQ ID NO: 8) and the probe for TAQMAN™ 5' FAM-AAGGGCATCCTGGGCTACACTGAGCA3' TAMRA (SEQ ID NO: 9).

These reference primers for RNA and DNA can be replaced by any housekeeping unique gene. The results given below were calculated using arbitrary quantities expressed either as CT (cycle threshold numbers) or $2^{\Delta CT}$ values (for instance $2^{CT}$ of hTERT$^{-CT}$ of b-Globin). They always compared extractions of plasma nucleic acids of cancer patients and healthy donors extracted the same day and with the same amount (0.5 ml) of plasma/serum. It is possible to estimate in another way by comparing the results to a curve obtained by known quantities of one gene.

The QuantiTect Probe RT-PCR (Qiagen) was used in 25 μl RT-PCR reaction mixture containing the manufacturer's Master Mix, the RT mix (Onmiscript™ reverse transcriptase, Sensiscript™ reverse transcriptase, hot-start Taq™ DNA polymerase) to which we added the set of primers (0.4 μM) and TAQMAN™ probe (0.1 μM) and 3 to 6 μl of the 30 μl of eluted nucleic acids. The RT-PCT conditions of the mixture were an initial incubation at 50° C. for 30 min followed by a 95° C. incubation for 15 min to activate the HotstarTaq™ DNA Polymerase, then 50 cycles at 94° C. (15 sec), 60° C. (1 min).

All base sequences mentioned here above as primer examples are known and may as such be consulted on the web site of the Genome Database. They may be replaced by other primers and probes located on the above-mentioned genes. Reference genes may be changed by other genes.

Results Obtained:

Data have been obtained on 74 cancer patients and 51 controls with 98% specificity. The sensitivity changes from cancer to cancer ranging from 81% to over 90%. The cancer patients suffered from head and neck, breast, colorectal, pancreatic and liver cancers.

The results obtained by Real Time Quantitative RT PCR measuring both DNA and RNA of hTERT compared to beta-Globin gene in the plasma of cancer patients and healthy controls are presented on the following Table.

| Samples studied | Number of samples | hTERT positive % |
|---|---|---|
| CONTROLS | 51 | 2% |
| PANCREATIC CANCER | 27 | 81% |
| HEAD AND NECK | 16 | 94% |
| COLORECTAL | 18 | 83% |
| BREAST | 7 | 100% |
| LIVER | 6 | 83% |

Furthermore, the results obtained are illustrated on the annexed figures, where;

Figure 1:
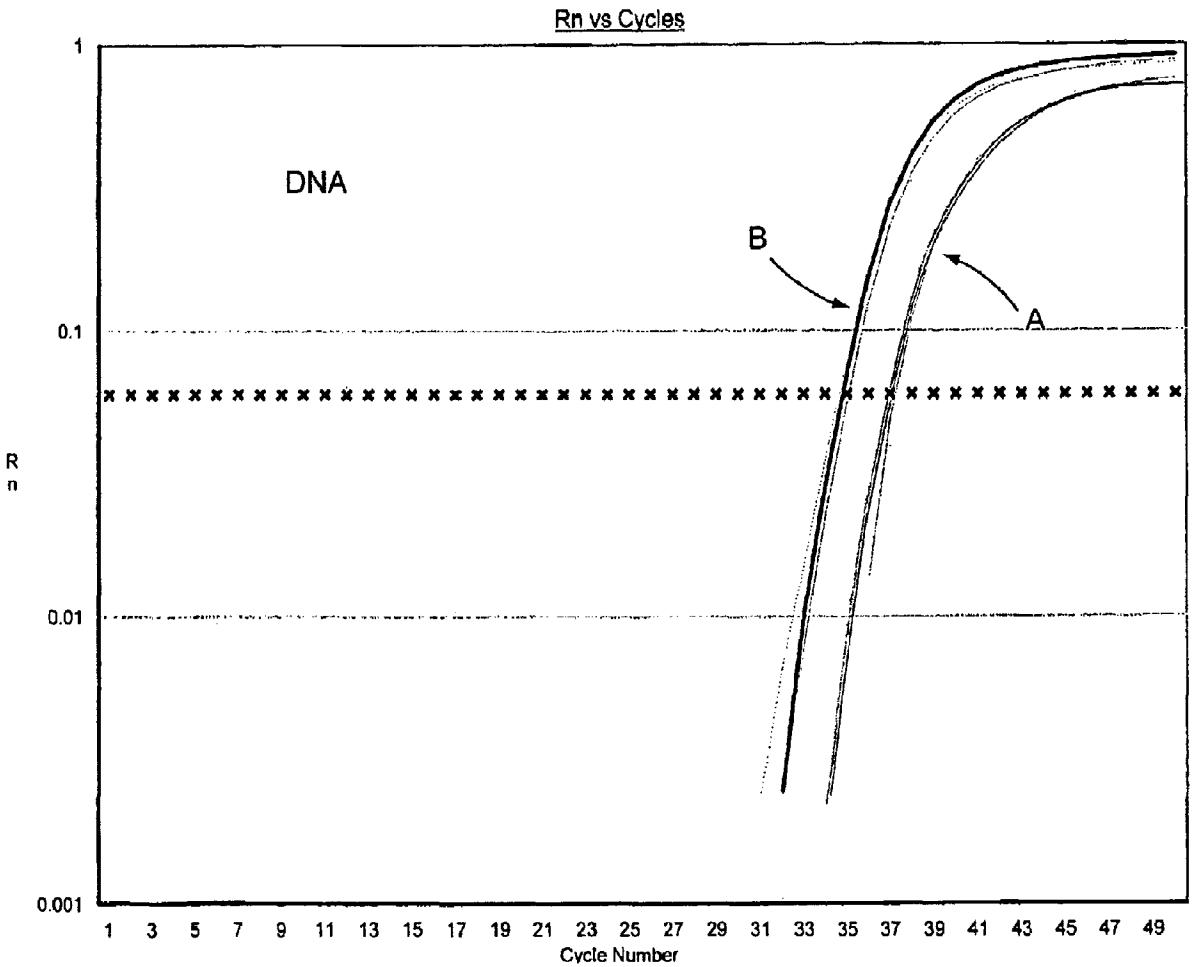
FIG. 1 shows as reference the amplification plots obtained using real time quantitative PCR for the hTERT gene (DNA), and with the x-axis being the cycle number of the PCR reaction and the y-axis the fluorescence intensity over background.

As it can easily be seen on FIG. 1, the first group of lines (A) with a CT value around 37 is composed of the amplification product of samples of DNA from healthy donors with hTERT primers, and the second group (B) with a CT value around 35 is composed of the amplification product of samples of plasma DNA from patients suffering from head and neck cancer.

Figure 2:
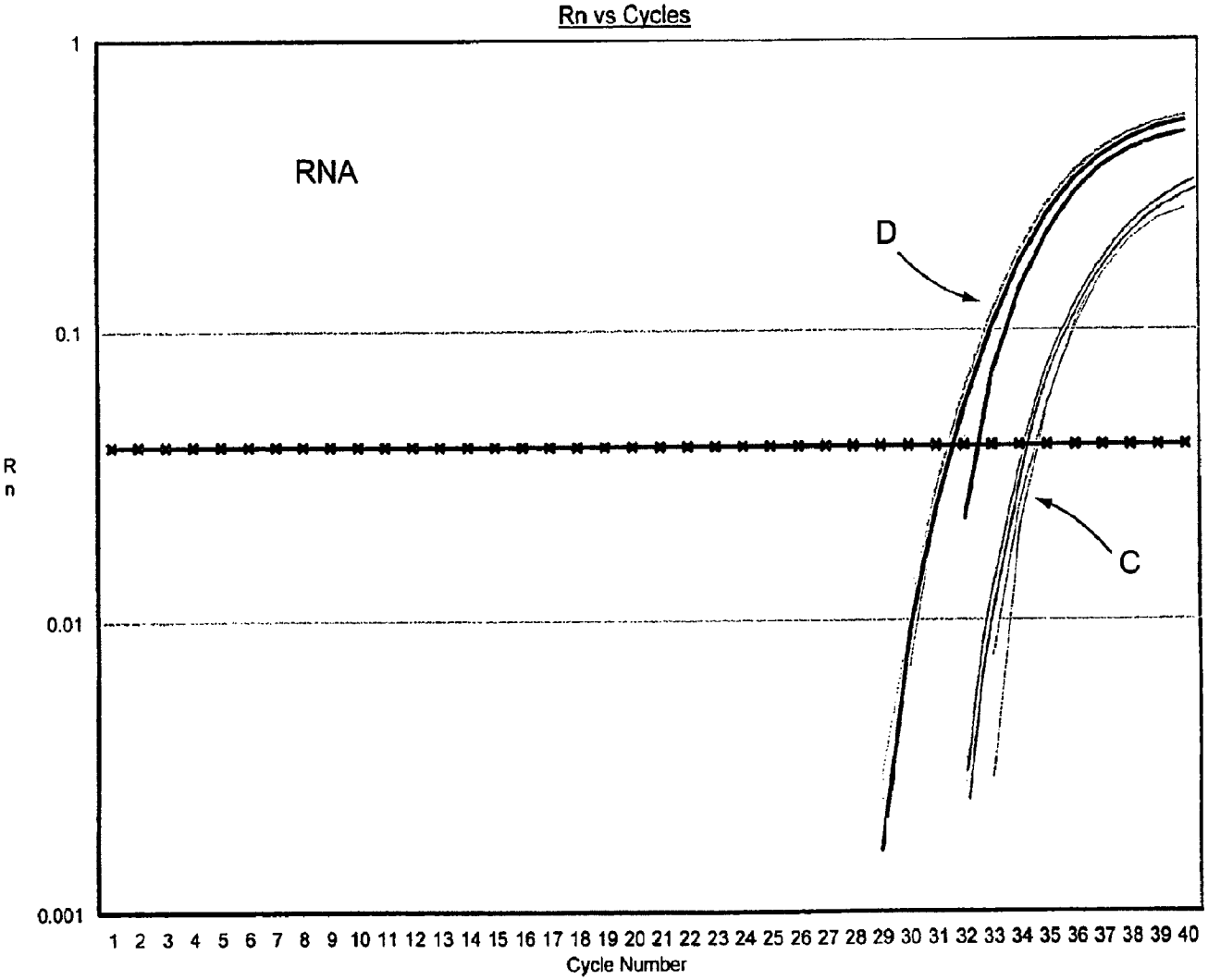
FIG. 2 shows as reference the amplification plots obtained using real time quantitative RT-PCR for the hTERT gene (RNA), and with the x-axis being the cycle number of the PCR reaction and the y-axis the fluorescence intensity over background.

On FIG. 2, the first group of lines (C) with a CT value around 34 is composed of the amplification product of samples of RNA from healthy donors with hTERT primers, and the second group (D) with a CT value around 32 is composed of the amplification product of samples of plasma RNA from patients suffering from head and neck cancer. A difference of 2 CT values represents a difference of 4 times RNA values obtained from the same amount of plasma.

Figure 3:
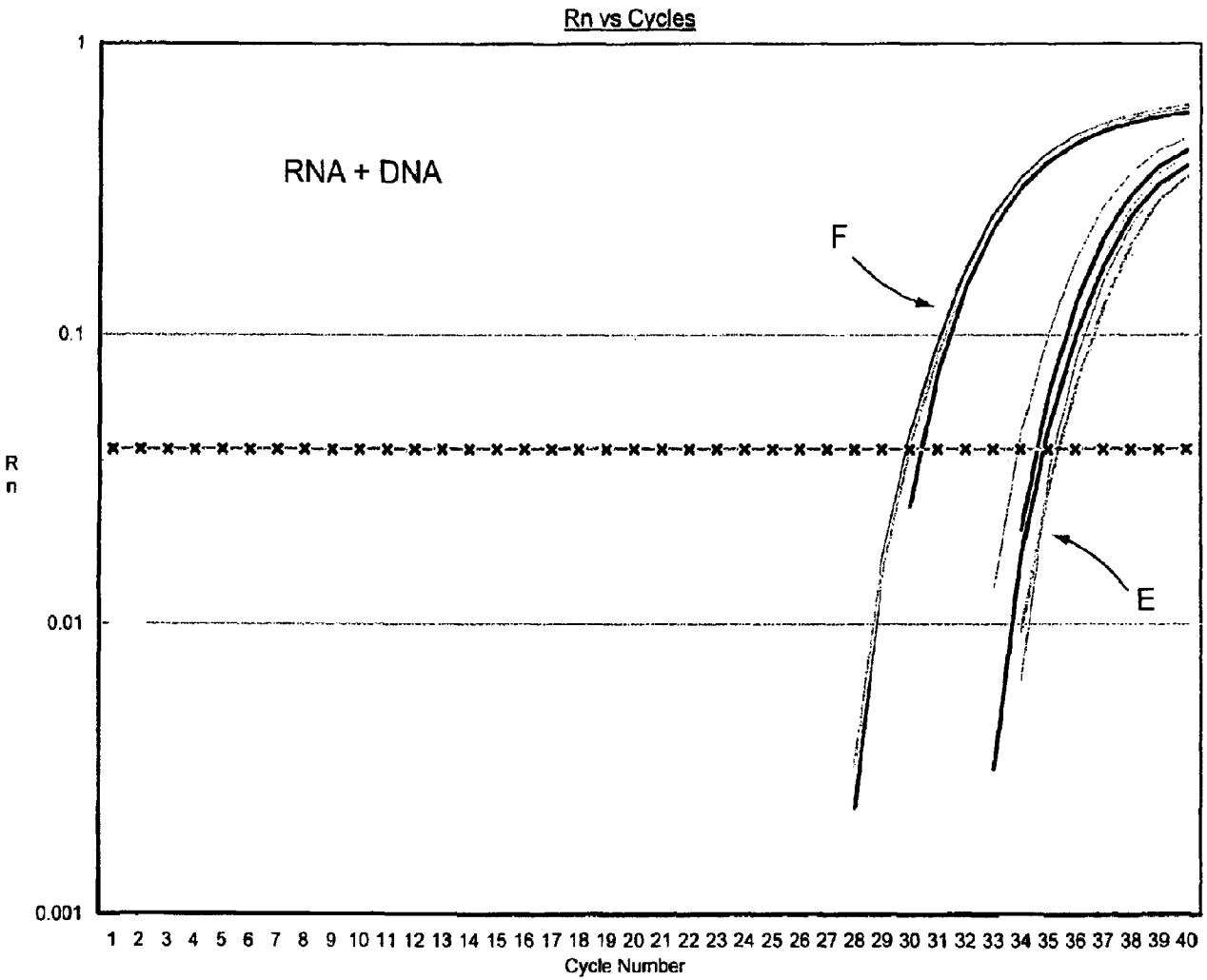
FIG. 3 shows the amplification plots obtained using real time quantitative RT-PCR for the hTERT gene (total nucleic acids DNA and RNA), according to the present invention, and with the x-axis being the cycle number of the PCR reaction and the y-axis the fluorescence intensity over background.

On FIG. 3, which represents the results of the method according to the present invention, the first group of lines (E) with a CT value around 35 is composed of the amplification product of samples of plasma nucleic acid from healthy donors with hTERT primers, and the second group (F) with a CT value around 29 is composed of the amplification product of samples of plasma nucleic acid from patients suffering from head and neck cancer. The difference between the CT values (comprising RNA and DNA) of the control group and the cancer group is higher than in FIGS. 1 and 2, DNA or RNA are measured. This demonstrates the clear advantage of the method according to the present invention.

SEQUENCE LISTING

```
<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1

accgtctgcg tgaggagatc                                                20


<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

ccggtagaaa aaagagcctg ttc                                            23
```

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
probe

<400> SEQUENCE: 3 tgtacgtcgt cgagctgctc aggtcttt 28

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 4 ctgctggtgg tctacccttg 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 5 cctgaagttc tcaggatcca 20

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
probe

<400> SEQUENCE: 6 ctcctgatgc tgttatgggc aaccct 26

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 7 gtggacctga cctgccg 17

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 8 ggaggagtgg gtgtcgc 17

-continued

```
<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9

aagggcatcc tgggctacac tgagca                                          26
```

The invention claimed is:

1. A method for the diagnosis or the follow up of the evolution of cancers which comprises measuring both gene over-expression (RNA) and gene amplification (DNA) of a gene [present] in [the] *a sample derived from* bodily [fluids of] *fluid from* a patient, that is both amplified and over-expressed in cancer cells and comparing to healthy controls, *wherein the sample is cell free or substantially cell free.*

2. The method according to claim 1, wherein *the* RNA and *the* DNA are extracted from [a] *the* bodily fluid, purified and amplified, and the over-expressed RNA and *the* amplified DNA are analyzed and compared to a house keeping gene.

3. The method according to claim 2, wherein the [genes] *gene* analyzed [are] *is* selected from hTERT, hTR, TEP1, MYCN, MYCC, ErbB2, Her2, Her2/Neu, Her 1, Cyclin A and D1, ABL, SKP2, ETV6 (TELgene), MGC2177, PLAG1, PSMC6P and LYN.

4. The method according to claim 2, wherein the [nucleic acids] *RNA and the DNA* are amplified by reverse transcriptase chain reaction (RT-PCR).

5. The method according to claim 3, wherein the [nucleic acids] *RNA and the DNA* are amplified by reverse transcriptase chain reaction (RT-PCR).

6. The method according to claim 1, wherein the [genes analyzed are] *gene measured is* selected from the group consisting of hTERT, hTR, TEP1, MYCN, MYCC, ErbB2, Her2, Her2/Neu, Her 1, Cyclin A and D1, ABL, SKP2, ETV6 (TELgene), MGC2177, PLAG1, PSMC6P and LYN.

7. The method according to claim 6, wherein the [nucleic acids] *RNA and the DNA* are amplified by reverse transcriptase chain reaction (RT-PCR).

8. The method according to claim 1, wherein the [nucleic acids] *RNA and the DNA* are amplified by reverse transcriptase chain reaction (RT-PCR).

9. The method according to claim 1, wherein the [genes analyzed are] *gene measured is* compared to a reference nucleic acid extract (DNA and RNA) corresponding to [the] expression (RNA) and quantity (DNA) of a house keeping gene.

10. The method according to claim 1, wherein the [genes analyzed are] *gene is* compared to a reference RNA corresponding to [the] expression of a house keeping gene.

11. The method according to claim 1, wherein the [genes analyzed are] *gene is* compared to a reference DNA corresponding to a housekeeping gene.

12. The method according to claim 1, wherein the gene quantification may be estimated in reference to a standard curve obtained with nucleic acids of a cell line.

13. The method according to claim 1, wherein the [nucleic acids] RNA and *the* DNA are analyzed by gel coloration, by radioactive immunological technique (RIA), by enzyme linked immunosorbant test (ELISA) or by a microchip test (gene array), and quantified by any method for nucleic acid quantification.

14. The method according to claim 1, wherein the [nucleic acids] RNA [and DNA are] *is* quantified by real time [RT PCR] *RT-PCR.*

15. The method according to claim 1, wherein the RNA and *the* DNA are extracted from the patient and measured simultaneously.

16. A method for measuring both gene over-expression (RNA) and gene amplification (DNA) in a patient suspected of having cancer, wherein the gene *measured* is selected from the group consisting of hTERT, hTR, TEP1, MYCN, MYCC, ErbB2, Her2, Her2/Neu, Her 1, Cyclin A, Cyclin D1, ABL, SKP2, ETV6 (TELgene), MGC2177, PLAG1, PSMC6P and LYN, comprising: obtaining a sample [of] *derived from* a bodily fluid from a patient, [and] *wherein the sample is cell free or substantially cell free,* extracting both RNA and DNA simultaneously from said sample, measuring both gene over-expression (RNA) and gene amplification (DNA) at the same time [in said sample] *from the extracted RNA and DNA*, and comparing said measurement to a healthy control.

17. The method according to claim 16, wherein *the* RNA and *the* DNA are extracted from [a] *the* bodily fluid, purified and amplified, and the over-expressed RNA and *the* amplified DNA are analyzed and compared to a house keeping gene.

18. The method according to claim 17, wherein the over-expressed and amplified gene is hTERT.

19. The method according to claim 18, wherein the [nucleic acids are] *RNA is* amplified by reverse transcriptase *polymerase* chain reaction (RT-PCR).

20. The method according to claim 16, wherein the [genes analyzed are] *gene measured is* compared to a reference nucleic acid extract (DNA and RNA) corresponding to the expression (RNA) and quantity (DNA) of a house keeping gene.

21. The method according to claim 16, wherein the [genes] *gene* analyzed [are] *is* compared to a reference RNA corresponding to the expression of a house keeping gene.

*22. The method according to claim 1, wherein said sample is selected from plasma, serum, saliva, and sputum.*

*23. The method according to claim 16, wherein said sample is selected from plasma, serum, saliva, and sputum.*

*24. The method according to either claim 1 or 16, wherein said RNA and said DNA from said bodily fluid comprise extracellular RNA and DNA.*

*25. The method according to either claim 1 or 16, wherein said measuring comprises amplifying both of said RNA and said DNA by polymerase chain reaction.*

*26. The method according to claim 25, wherein said amplifying further comprises using a single primer/probe set to amplify both of said DNA and said RNA.*

*27. A method for the diagnosis or the follow up of the evolution of cancers which comprises measuring both the quantity of gene expression (RNA) and quantity of gene amplification (DNA) of one or more genes in a sample derived*

*from a bodily fluid of a patient, wherein said sample is cell free or substantially cell free, and comparing to healthy controls.*

*28. The method according to claim 27, wherein said measuring comprises extracting both of said RNA and said DNA from said bodily fluid, purifying said extracted RNA and said extracted DNA, amplifying said purified RNA and said purified DNA, analyzing said amplified RNA and said amplified DNA, and comparing to a house keeping gene.*

*29. The method according to claim 28, wherein said amplifying comprises using polymerase chain reaction.*

*30. The method according to claim 28, wherein said amplifying comprises using a single primer/probe set to amplify both of said RNA and said DNA.*

*31. The method according to claim 27, wherein said comparing comprises comparing to a reference nucleic acid extract corresponding to expression (RNA) and/or quantity (DNA) of a house keeping gene.*

*32. The method according to claim 27, wherein said measuring comprises estimating said one or more genes in reference to a standard curve obtained with nucleic acids of a cell line.*

*33. The method according to claim 27, further comprising analyzing said RNA and said DNA by gel coloration, by radioactive immunological technique (RIA), by enzyme linked immunosorbant test (ELISA) or by a microchip test (gene array), and quantifying by any method for nucleic acid quantification.*

*34. The method according to claim 27, further comprising extracting both of said RNA and said DNA from the patient and measuring simultaneously.*

*35. The method according to claim 27, wherein said sample is selected from plasma, serum, saliva, and sputum.*

*36. The method according to claim 27, wherein both of said RNA and said DNA comprise extracellular RNA and extracellular DNA.*

*37. The method according to claim 1 or 16 further comprising providing a diagnosis and/or follow up as to the evolution of said cancer.*

*38. The method of claim 1, wherein the measuring is performed using a microchip.*

*39. The method of claim 16, wherein the measuring is performed using a microchip.*

*40. The method of claim 27, wherein the measuring is performed using a microchip.*

*41. The method of claim 1, further comprising identifying if the patient is in need of treatment if there is an increased level in the sample as compared to the healthy controls.*

*42. The method of claim 16, further comprising identifying if the patient is in need of treatment if there is an increased level in the sample as compared to the healthy controls.*

*43. The method of claim 27, further comprising identifying if the patient is in need of treatment if there is an increased level in the sample as compared to the healthy controls.*

*44. The method of claim 41, further comprising providing treatment to the identified patient.*

*45. The method of claim 42, further comprising providing treatment to the identified patient.*

*46. The method of claim 43, further comprising providing treatment to the identified patient.*

* * * * *